US008192735B2

(12) United States Patent
Breit et al.

(10) Patent No.: US 8,192,735 B2
(45) Date of Patent: Jun. 5, 2012

(54) METHOD FOR MODULATING APPETITE

(75) Inventors: Samuel Norbert Breit, Gordon (AU); Asne Rhoda Bauskin, Bondi Junction (AU)

(73) Assignee: St Vincent's Hospital Sydney Limited, New South Wales (AU)

( * ) Notice: Subject to any disclaimer, the term of this patent is extended or adjusted under 35 U.S.C. 154(b) by 1589 days.

(21) Appl. No.: 11/547,675

(22) PCT Filed: Apr. 13, 2005

(86) PCT No.: PCT/AU2005/000525
§ 371 (c)(1),
(2), (4) Date: Oct. 6, 2006

(87) PCT Pub. No.: WO2005/099746
PCT Pub. Date: Oct. 27, 2005

(65) Prior Publication Data
US 2009/0004181 A1 Jan. 1, 2009

(30) Foreign Application Priority Data

Apr. 13, 2004 (AU) ............................. 2004901957

(51) Int. Cl.
*A61K 39/00* (2006.01)
*A61K 39/395* (2006.01)
*G01N 33/53* (2006.01)
*C12Q 1/68* (2006.01)

(52) U.S. Cl. ............... 424/130.1; 424/133.1; 424/141.1; 514/4.8; 514/4.9; 435/6; 435/7.1

(58) Field of Classification Search ........................ None
See application file for complete search history.

(56) References Cited

U.S. PATENT DOCUMENTS 7,141,661 B2 * 11/2006 Eling et al. .................... 536/23.2
7,157,235 B2 *  1/2007 Breit et al. ..................... 435/7.1
7,514,221 B2 *  4/2009 Breit et al. ..................... 435/7.1

FOREIGN PATENT DOCUMENTS

WO WO 99/06445 A1 2/1999
WO WO 01/81928 A1 11/2001

OTHER PUBLICATIONS

Brown D A, et al., Clin Cancer Res 9:2642-2650 (2003).*
Albertoni et al. Oncogene 2002: 27:4212-4219.*
Liu et al., Cancer Res 2003:63:5034-5040.*
Baek et al. Mol Pharmacol 2001: 59:901-908.*
Lee et al., Cancer Res 2003: Aug. 1; 63(15):4648-4655.*
Brown et al., Clinical Cancer Research 2003: 9:2642-2650.*
Supplementary European Search Report; European Application No. 05729508.1-2402 / 1734986 PCT/AU2005/000525; dated Jun. 22, 2009 (4 pgs).
Welsh, J.B., et al; "Large-scale delineation of secreted protein biomarkers overexpressed in cancer tissue and serum"; *PNAS*; vol. 100, No. 6, Mar. 18, 2003, pp. 3410-3415 (XP-002993660).
Rubin, Harry; "Cancer cachexia: Its correlations and causes"; *PNAS*; vol. 100, No. 9, Apr. 29, 2003, pp. 5384-5389 (XP 009117770).
Strelau, J., et al; "GDF-15/MIC-1 a novel member of the TGF-beta superfamily"; *J. Neural. Transm. Suppl.*; 2000, vol. 60, pp. 273-276.
Form PCT/IB/373; PCT Notification Concerning Transmittal of International Preliminary Report on Patentability; International Application No. PCT/AU2005/000525, filed Apr. 13, 2005 (2 pgs).
Form PCT/ISA/237, PCT Written Opinion of the Int'l Searching Authority (3 pgs), Jul. 11, 2005.

* cited by examiner

*Primary Examiner* — Daniel C Gamett
(74) *Attorney, Agent, or Firm* — Nixon & Vanderhye

(57) ABSTRACT

Method of modulating appetite and/or body weight in a subject by administering to the subject an effective amount of a MIC-1 modulating agent. The agent is selected from (i) MIC-1 inhibiting agents which decrease the amount of endogenous MIC-1 in the subject, (ii) MIC-1 inhibiting agents which inhibit the activity of endogenous MIC-1 in the subject, (iii) MIC-1 enhancing agents which enhance the amount of endogenous MIC-1 in the subject, and (iv) MIC-1 enhancing agents which enhance the activity of endogenous MIC-1 in the subject.

11 Claims, 17 Drawing Sheets

Mouse weight after injection of 0.1 mg of MAb on day 11

Number of days after DU145 injection

Mouse weight after injection of 0.3 mg of MAb on day 11

Number of days after DU145 injection

Mouse weight after injection of 1 mg of MAb on day 11

Number of days after DU145 injection

Tumour growth in mice injected with DU145 cells
(received 0.1 mg Mab on day 11)

Number of days after DU145 injection

Mouse weight after injection of PBS only on day 11

Number of days after DU145 injection

Mouse weight – not treatment at day 11

Number of days after DU145 injection

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: consensus sequence for proconvertase
<220> FEATURE:
<221> NAME/KEY: MISC_FEATURE
<222> LOCATION: (2)..(3)
<223> OTHER INFORMATION: Xaa = any amino acid

<400> SEQUENCE: 1

Arg Xaa Xaa Arg
1

<210> SEQ ID NO 2
<211> LENGTH: 7
<212> TYPE: PRT
<213> ORGANISM: Artificial Sequence
<220> FEATURE:
<223> OTHER INFORMATION: sequence including furin-like proconvertase
      site

<400> SEQUENCE: 2

Arg Gly Arg Arg Arg Ala Arg
1               5

METHOD FOR MODULATING APPETITE

This application is the U.S. National Phase of International Application PCT/AU2005/000525, filed 13 Apr. 2005, which designated the U.S. PCT/AU2005/000525 claims priority to Australian Application No. 2004901957 filed 13 Apr. 2004. The entire content of these applications are incorporated herein by reference.

FIELD OF THE INVENTION

The invention relates to a method for modulating appetite and/or body weight in an individual. In one particular application, the method involves administering to a subject suffering from decreased appetite and/or weight loss associated with late stage tumours (particularly, cancers), an effective amount of an agent which is capable of decreasing the amount of macrophage inhibitory cytokine-1 (MIC-1) present in the subject or which otherwise inhibits the activity of MIC-1 in the subject.

BACKGROUND TO THE INVENTION

The control of body weight is a complex process that at present is incompletely understood. It is multifactorial and is influenced by appetite, food ingestion and excretion, energy utilisation and expenditure. A number of soluble mediators are known to be involved in regulating various aspects of this process and include hormones and cytokines such as leptin, ghrelin, melanocortin, agouti-related peptide, and neuropeptide Y (NPY). Normal weight control is important to good health and obesity especially, may greatly increase morbidity and mortality in individuals. Lower than average weight can also be problematic, and in developed societies, where sufficient food is available, this is more frequently due to diseases including some chronic inflammatory disorders, eating disorders such as anorexia nervosa, and cancer. Especially in the late stages of cancer, cachexia is common (occurring in most terminally ill cancer patients), and is responsible for about a quarter of all cancer-related deaths.

Some years ago, the present applicant cloned and characterised a novel human TGF-β superfamily cytokine that was named macrophage inhibitory cytokine-1 (MIC-1) (1-7), but has since also become known as prostate derived factor (PDF), placental bone morphogenetic protein (PLAB), and growth/differentiation factor-15 (GDF-15) (7). Under resting conditions, placenta is the only tissue expressing large amounts of MIC-1 (7), but epithelial cells in a wide variety of other organs also normally express small amounts of MIC-1 mRNA. This low level of normal MIC-1 expression is, however, dramatically increased in malignancy, inflammation and injury (7, 8-11), the increase being induced by a wide variety of cell stress and activation factors, and is mediated intracellularly, particularly by the transcription factor p53 and EGR-1 (12-15). In particular, increased MIC-1 expression has been strongly linked to breast, prostate, pancreatic and colon cancers (9-11, 17, 18), and in a recently published study (20) of several hundred patients with colonic polyps or colon cancer, the present applicant showed that elevation of serum levels of MIC-1 occurs in a progressive stepwise manner, reflecting colon cancer pathogenesis, with progression from normal to benign and then to dysplastic colonic polyps and finally colon cancer. This observation, along with results from other studies (15, 17, 19, 21), suggests that MIC-1 has an important role in tumour progression, by inducing significant paracrine effects modulating the tumour environment.

In work leading to the present invention, it had been observed that the serum levels of MIC-1 of patients in the late stages of one of the abovementioned epithelial cancers (eg serum levels of 10 to 50 ng/ml or more), correlated with serum levels in mice which were over-expressing MIC-1 and which showed marked weight loss. It was therefore proposed that the cachexia commonly exhibited in patients with cancer associated with increased MIC-1 expression, is due to the over-expression of MIC-1 and that by inhibiting that expression (eg with anti-MIC-1 antibodies), it would be possible to reverse or reduce the severity of the weight loss.

SUMMARY OF THE INVENTION

Thus, in a first aspect, the present invention provides a method of modulating appetite and/or body weight in a subject, said method comprising administering to said subject an effective amount of a MIC-1-modulating agent, wherein said agent increases or decreases the amount of MIC-1 present in said subject, or inhibits or enhances the biological activity of MIC-1 present in said subject.

In a second aspect, the present invention provides a method for increasing appetite and/or body weight in a subject, said method comprising administering to said subject an effective amount of a MIC-1-inhibiting agent optionally in admixture with a pharmacologically-acceptable carrier and/or excipient.

In a third aspect, the present invention provides a method for decreasing appetite and/or body weight in a subject, said method comprising administering to said subject an effective amount of a MIC-1-enhancing agent optionally in admixture with a pharmacologically-acceptable carrier and/or excipient.

DETAILED DESCRIPTION OF THE INVENTION

Figure 1:
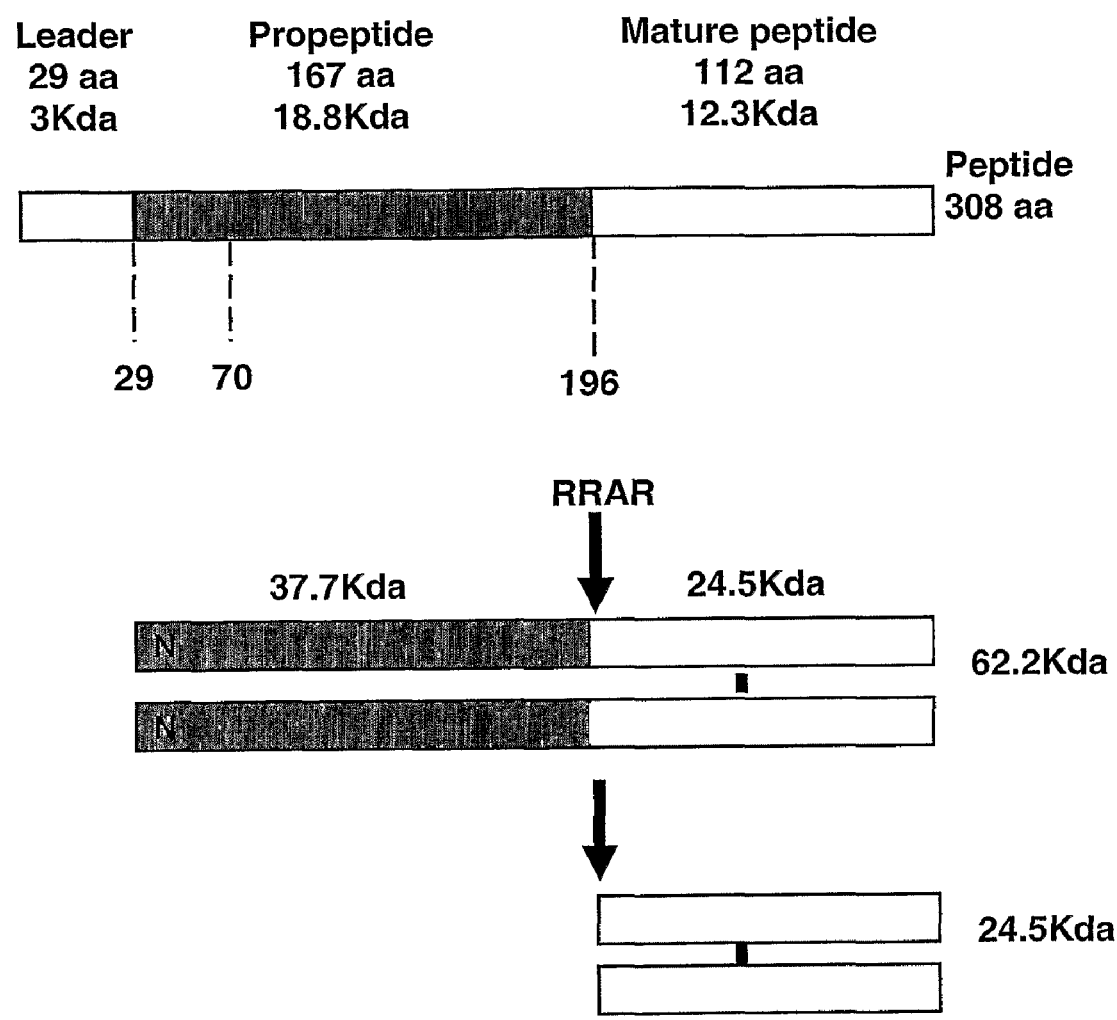
FIG. 1 provides a schematic diagram of the processing of the MIC-1 precursor through to its mature, 112 amino acid form. Cleavage of the propeptide from the mature domain occurs at $Arg^{196}$.

It had been previously found that many cancers, especially of epithelial origin, over-express MIC-1 and that serum MIC-1 levels rise in patients with these cancers in proportion to the stage and extent of the disease. Especially in late stages of cancer, these serum levels can reach 10 to 50 ng/ml or more, levels which in mice are associated with marked weight loss. By reducing MIC-1 levels or the activity of MIC-1 in cancer patients, it is expected that weight loss, and the subsequent ill-effects on patient well-being and esteem, may be reversed or reduced. In turn, this may assist in the patient's capacity to be treated for cancer and positively respond to the therapy, and thereby reduce morbidity and mortality.

Thus, in a first aspect, the present invention provides a method of modulating appetite and/or body weight in a subject, said method comprising administering to said subject an effective amount of a MIC-1-modulating agent, wherein said agent increases or decreases the amount of MIC-1 present in said subject, or inhibits or enhances the biological activity of MIC-1 present in said subject.

Where the method is operated to decrease the amount of MIC-1 present in the subject (particularly, to decrease the serum level of MIC-1), or inhibit the activity of MIC-1, the method may increase appetite and/or lead to an increase in body weight or, at least, a reduction in any loss of body weight in the subject. On the other hand, where the method is operated to increase the amount of MIC-1 (particularly, to increase the serum level of MIC-1), or enhance the activity of MIC-1, the method may decrease appetite and/or lead to a decrease in body weight or, at least, a reduction in any gain of body weight in the subject.

In a second aspect, the present invention provides a method for increasing appetite and/or body weight in a subject, said method comprising administering to said subject an effective amount of a MIC-1-inhibiting agent optionally in admixture with a pharmacologically-acceptable carrier and/or excipient.

The method of the second aspect involves the administration of a MIC-1-inhibiting agent. Such an agent may decrease the amount of endogenous MIC-1 in the subject (particularly, the serum level of endogenous MIC-1), and may be selected from anti-MIC-1 antibodies or fragments thereof (eg Fab fragments or recombinant scFv fragments (22)), catalytic and inhibitory oligonucleotide molecules targeted against the MIC-1 gene (eg ribozymes, DNAzymes, antisense RNA, and small inhibitory RNA (siRNA)), and inhibitors of MIC-1 transcription or translation. Alternatively, the MIC-1-inhibiting agent may inhibit the activity of endogenous MIC-1 in the subject, and may be selected from anti-MIC-1 antibodies or fragments thereof (eg Fab fragments or recombinant scFv fragments), soluble extra-cytoplasmic receptor domains of MIC-1 receptors, other soluble molecules or matrix-associated proteins that bind to MIC-1 (eg heparin, heparan sulphate and fetuin), and peptide, peptide mimetic, or small organic molecule inhibitors of, for example, MIC-1 binding to its receptor. Additionally, peptide, peptide mimetic, or small organic molecule inhibitors might inhibit the activity of endogenous MIC-1 by inhibiting MIC-1 receptor phosphorylation, or transmission of signalling information from the MIC-1 receptor to the cell nucleus, or action of the relevant transcription factor(s) on the cell genome. Further, the MIC-1-inhibiting agent may be an inhibitor of the proconvertase enzyme responsible for cleaving the propeptide from the mature MIC-1 protein domain. As is shown in example 1 hereinafter, immature MIC-1 (ie proMIC-1) associates with the extracellular matrix, and thus by inhibiting the proconvertase enzyme responsible for processing of MIC-1, MIC-1 can be "locked up" in the extracellular matrix. Proconvertase enzyme may be inhibited by, for example, (a) transfection of cells with an alpha-1-antitrypsin mutant, alpha-1-antitrypsin Portland, (b) polyarginine peptides; and (c) peptides based on the sequence of the target protein for the proconvertase, spanning the propeptide sequence and proconvertase sequence of the target protein.

Preferably, the MIC-1-inhibiting agent is an anti-MIC-1 antibody or fragment thereof, and more preferably, a humanised monoclonal anti-MIC-1 antibody. Humanised anti-MIC-1 antibodies may be produced in accordance with the methods described in U.S. Pat. No. 5,225,539 (the entire disclosure of which is incorporated herein by reference).

The method of the second aspect is useful for the treatment of a subject suffering from decreased appetite and/or weight loss associated with inflammatory disease (eg rheumatoid arthritis) and/or cancer (particularly, an epithelial cancer such as breast, prostate, colonic, rectal, bladder and pancreatic cancer). The method, however, may also be useful for the treatment of decreased appetite and/or weight loss associated with any other disease, condition or treatment wherein MIC-1 is over-expressed (eg injury, inflammation, stress, and radiotherapy and chemotherapy). Subjects suitable for treatment with the method of the second aspect may be restricted to those showing MIC-1 over-expression or, at least, a serum level of MIC-1 consistently at the high end of the normal serum level of 200-1200 pg/ml. Such subjects can be selected by detection of a high serum MIC-1 level (eg from a whole blood or serum sample), using an assay for MIC-1 (eg a MIC-1 ELISA (4)).

Preferably, the method of the second aspect is used for the treatment of a subject suffering from decreased appetite and/or weight loss associated with advanced cancer, where a high total tumour mass often leads to a high serum level of MIC-1.

In a third aspect, the present invention provides a method for decreasing appetite and/or body weight in a subject, said method comprising administering to said subject an effective amount of a MIC-1-enhancing agent optionally in admixture with a pharmacologically-acceptable carrier and/or excipient.

The method of the third aspect involves the administration of a MIC-1-enhancing agent. Such an agent may increase the amount of endogenous MIC-1 in a subject (particularly, the serum level of endogenous MIC-1), and may be selected from MIC-1, and agents which enhance transcription or translation of the MIC-1 gene (eg the p53 transcription factor, which is often seen in elevated levels in diseases associated with MIC-1 over-expression, or agents which enhance p53 expression or activity such as nutlin (23)). Alternatively, the MIC-1-enhancing agent may enhance the activity of endogenous MIC-1 in the subject. As used herein, the term MIC-1-enhancing agent is to be regarded as including agents which mimic the activity of MIC-1 (eg active MIC-1 fragments, peptide mimetics of the active domains of MIC-1, and small organic molecules which mimic MIC-1 activity).

The method of the third aspect is useful for the treatment of a subject suffering from obesity or who might otherwise desire weight loss for reasons of well-being or vanity.

MIC-1-modulating agents for use in the methods of the present invention may be formulated into any suitable pharmaceutical/veterinary composition or dosage form (eg compositions for oral, buccal, nasal, intramuscular and intravenous administration). Typically, such a composition will be administered to the subject in an amount which is effective to modulate appetite and/or body weight, and may therefore provide between about 0.01 and about 100 µg/kg body weight per day of the MIC-1-modulating agent, and more preferably providing from 0.05 and 25 µg/kg body weight per day of the MIC-1-modulating agent. A suitable composition may be intended for single daily administration, multiple daily administration, or controlled or sustained release, as needed to achieve the most effective results.

In addition to the MIC-1-modulating agents identified above, other MIC-1-modulating agents may be identified by screening candidate agents or libraries of agents for an effect on the amount of MIC-1 present in a subject and/or on the activity of MIC-1. In a similar manner, agents for treatment of various diseases or conditions could be assessed for undesirable side-effects on appetite and/or body weight (eg undesirable suppression or enhancement of appetite).

Thus, in a further aspect, the present invention provides a method for assessing the effect of an agent on the appetite and/or body weight of a subject, said method comprising administering said agent to said subject or a suitable animal model thereof (eg a mouse), and detecting any increase or decrease in the amount of MIC-1 (particularly, the serum MIC-1 level) in said subject or animal model.

Any increase or decrease in the amount of MIC-1 in the subject or animal model may be identified by obtaining MIC-1 samples (eg whole blood or serum samples) before and after the administration of said agent, and determining the respective amount of MIC-1 in said samples (eg with a MIC-1 ELISA).

In a similar aspect, the present invention provides a method for assessing the effect of an agent on the appetite and/or body weight of a subject, said method comprising forming a mixture between MIC-1 (or a functional fragment or mimetic thereof), a MIC-1 binding partner (preferably, a MIC-1 receptor or functional fragment or mimetic thereof), and said agent, and detecting any increase or decrease in binding between the MIC-1 (or functional fragment or mimetic thereof) and the MIC-1 binding partner.

An increase in binding may indicate that the agent is likely to decrease appetite and/or body weight of a subject. On the other hand, a decrease in binding may indicate that the agent is likely to increase appetite and/or body weight of a subject.

Also, in a further similar aspect, the present invention provides a method for assessing the effect of an agent on the appetite and/or body weight of a subject, said method comprising exposing a cell expressing MIC-1 to said agent and detecting any increase or decrease in the level of said expression of MIC-1.

An increase in expression of MIC-1 may indicate that the agent is likely to decrease appetite and/or body weight of a subject. On the other hand, a decrease in expression of MIC-1 may indicate that the agent is likely to increase appetite and/or body weight of a subject.

Preferably, this method is conducted in vitro using a MIC-1 expressing cell or cell line selected from macrophages, epithelial cells, endothelial cells and cell lines thereof.

In a still further aspect, the present invention provides a method of assessing appetite in a subject, said method comprising determining the amount of MIC-1 (particularly, the serum MIC-1 level) present in said subject.

Such a method may also be predictive of future body mass.

The finding that MIC-1 over-expression appears to decrease appetite and/or body weight in a subject, suggests that methods of gene therapy to increase the level of MIC-1 in a subject may provide an effective treatment of obesity. Therefore, the present invention also contemplates gene therapy methods, and gene therapy agents, for decreasing appetite and/or body weight in a subject, comprising recombinant MIC-1 genes to bring about increased endogenous MIC-1 expression. Vectors suitable for the introduction of MIC-1 genes include recombinant adenoviral or adenoviral-associated vectors, recombinant retroviral vectors, recombinant lentivirus vectors, liposomes including linear DNA, and transduced or transformed stem cells.

In order that the nature of the present invention may be more clearly understood, preferred forms thereof will now be described with reference to the following non-limiting examples.

EXAMPLE 1

Regulation of Serum MIC-1 Levels

MIC-1, like other members of the TGF-β superfamily of proteins, is synthesised as a precursor containing an N-terminal propeptide and a C-terminal mature MIC-1 domain. The precursor undergoes disulphide-linked dimerisation in the endoplasmic reticulum (ER) and, once dimerised, leaves the ER for the Golgi apparatus, where a furin-like convertase cleaves it at a conserved RXXR site (amino acid 196) (SEQ ID No: 1). This cleavage separates the propeptide from the mature C-terminal domain and MIC-1 is thus released as a 24.5 kD disulphide linked dimer (1)(FIG. 1).

It has been previously found that substantial amounts of MIC-1 are normally secreted in an unprocessed form. For example, it has been found that endogenous unprocessed proMIC-1 is secreted from a variety of cells including the trophoblast cell line BeWo (4), the prostate cancer cell lines LnCAP and PC3, the pancreatic cell line Panc 1 and the monocytoid cell line U937. In the prostate adenocarcinoma line, LnCAP, it has been found that unprocessed proMIC-1 associates with the extracellular matrix (ECM), whilst mature MIC-1 locates to the conditioned medium (24). Preliminary studies with MDCK transfectants has also demonstrated that ECM association is also mediated by a C-terminal region of the propeptide at amino acids 144-195. Additionally, both purified recombinant propeptide and proMIC-1 interact with heparin through the same C-terminal region of the propeptide.

The association of proMIC-1 with the ECM, suggests that ECM association may provide local storage of latent MIC-1, wherein processing of the stored proMIC-1 would result in the rapid release of mature MIC-1 (which has little affinity for ECM) into the circulation. To test this concept, a tumour xenograft model in nude mice (16) was developed.

Materials and Methods

Using the DU145 human prostate carcinoma line (17), which makes no endogenous MIC-1 (largely because the cells produce no functional p53) and is therefore useful as a vehicle for expressing various human MIC-1 constructs, permanently transfected and subcloned DU145 cell lines were generated which were transduced with eukaryotic expression vectors (IRES II EGFP vector, Clontech) containing sequences encoding either;
(i) full length human proMIC-1 (except using an FSH leader peptide, rather than the natural leader)(1),
(ii) mature human MIC-1 (no propeptide, but including an FSH leader),
(iii) human proMIC-1 (including an FSH leader) with a deletion of the amino acid sequence RGRRRAR (SEQ ID No:2) including the furin-like proconvertase site (shown in bold), thereby preventing processing and subsequent release of mature MIC-1 from the propeptide, and
(iv) vector only negative control (5).

High expressing subclones were selected based on EGFP expression. These cells were injected subcutaneously into the flank of immunodeficient BALB/c nu/nu nude mice. Mice were monitored regularly and their weight determined on a 2-3 daily basis. Mice were sacrificed about 2 months after injection or when tumour diameter reached 1.1 cm. Serum was obtained from these mice just prior to sacrifice, for estimation of the level of human MIC-1 by ELISA (4, 16, 18). This ELISA for human MIC-1 does not cross react with murine MIC-1, and has been previously used for the successful and exclusive measurement of human tumour MIC-1 levels in mice (16).

Results

Figure 2:
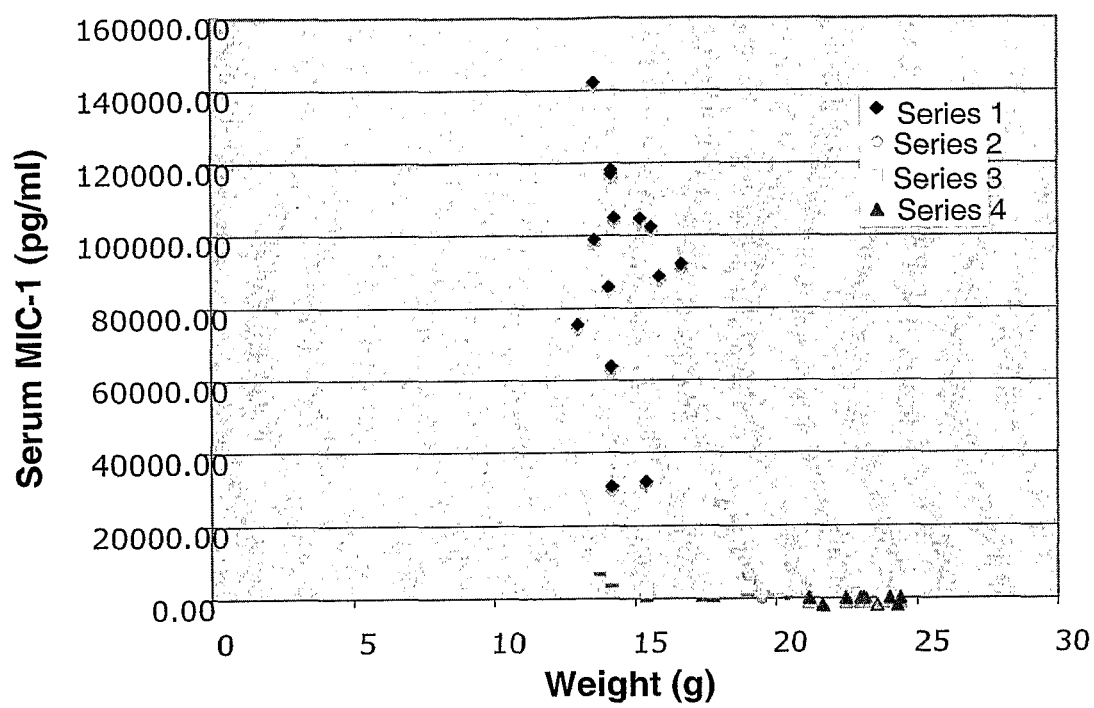
FIG. 2 graphically shows the relationship between nude mouse weight and human MIC-1 serum levels in blood collected when the largest of the mouse tumours has reached about 1 cm diameter. Nude mice were xenografted with human DU145 cells engineered to over express either;
(i) full length human MIC-1 (including the propeptide) (series 3),
(ii) mature human MIC-1 (no propeptide) (series 1),
(iii) human MIC-1 including the propeptide but having the furin-like proconvertase site deleted (FURIN DEL) (series 2), and
(iv) vector only negative control (series 4).
Figure 3:
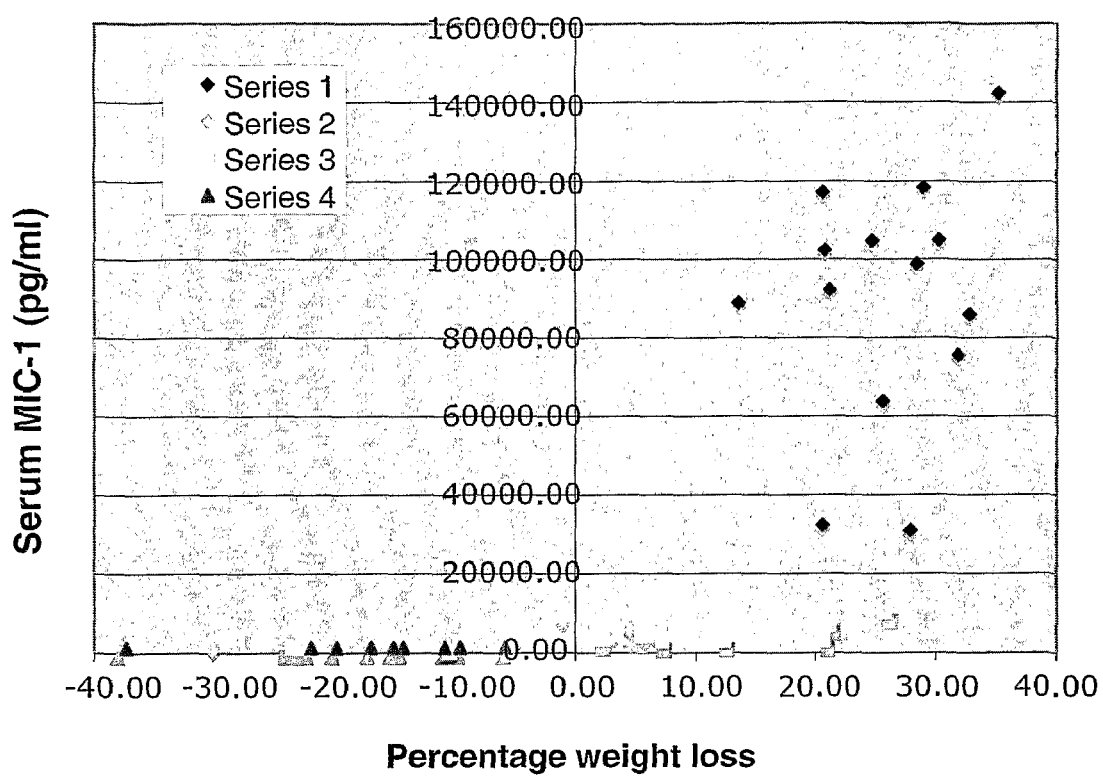
FIG. 3 graphically shows the relationship between nude mouse percentage weight loss (compared to weight at the start of the experiment) and human MIC-1 serum levels in blood collected when the largest of the mouse tumours had reached about 1 cm diameter. Nude mice were xenografted with human DU145 cells engineered to over express;
(i) full length human MIC-1 (including the propeptide) (series 3),
(ii) mature human MIC-1 (no propeptide) (series 1),
(iii) human MIC-1 including the propeptide but having the furin-like proconvertase site deleted (FURIN DEL) (series 2), and
(iv) vector only negative control (series 4).

The results are shown in FIGS. 2 and 3. Only tumour mice expressing mature MIC-1 showed a dramatically elevated level of serum MIC-1. Mouse tumours expressing the FURIN DEL mutant of MIC-1, which could not be processed normally and thus contained the propeptide, had markedly lower serum MIC-1 levels. By extrapolation from in vitro data, it appears that this result is due to tight association of the FURIN DEL mutant with the ECM.

Discussion

The results obtained in this example indicate that the MIC-1 propeptide is important in regulating the distribution of MIC-1 between tissues and blood. As such, any substances that bind to the MIC-1 propeptide (eg heparin and heparan sulphate), or otherwise compete with matrix binding sites on the propeptide (eg recombinant purified propeptide itself) would be expected to increase the level of MIC-1 in the circulation. As a consequence, functions mediated by serum MIC-1, including appetite, would be modulated.

EXAMPLE 2

Modulation of Appetite by MIC-1

Over the course of the investigation described in example 1, it was noted that of the xenograft model mice, those bearing a tumour over-expressing MIC-1, either lost weight, or did not gain as much weight as control mice. Studies were therefore conducted to determine the extent and reason for the observed effect on mice weight.

Materials and Methods

The mice were weighed just before sacrifice and weight/% weight loss compared against the measured serum MIC-1 levels (ie as determined by ELISA described in example 1).

To assess whether serum MIC-1 levels were responsible for observed weight loss, a second study was conducted wherein nude mice were injected subcutaneously with the DU145 clone over expressing mature human MIC-1 (and which we had previously associated with the highest serum MIC-1 levels) and at day 27, after the mice had lost substantial weight, injected intraperitoneally with either 1 mg or 10 mg of control purified sheep IgG or IgG purified from serum from sheep that had been immunised with recombinant human MIC-1 and had high titre antibodies to human MIC-1. This sheep anti-human MIC-1 IgG reacted with high affinity to human MIC-1 and had been previously used in a MIC-1 ELISA.

To further demonstrate that the observed weight loss was mediated by MIC-1 and not another tumour-derived product, an evaluation of weight loss was made of two transgenic mouse lines (min 28 and min 75; both created in C57B16 mice) which over express murine MIC-1 under the control of the macrophage specific c-fms promoter.

Results

Figure 4A:
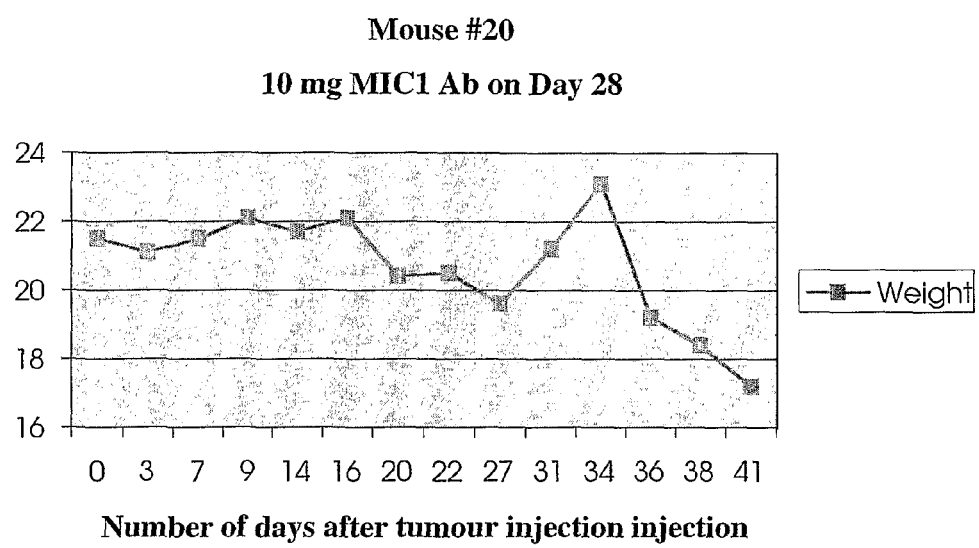
FIG. 4 provides graphical results of the effect of sheep antihuman MIC-1 antibodies on mouse weight (g). (A) On day 27, two mice were given 10 mg (intraperitoneally) of purified IgG from sheep immunised with highly purified recombinant MIC-1 to develop high titre antibodies to human MIC-1. (B) On day 27, two mice were give 10 mg (intraperitoneally) of control purified IgG from normal sheep serum. The graphs A and B show representative data from one of each of the mice in the two groups.
Figure 4B:
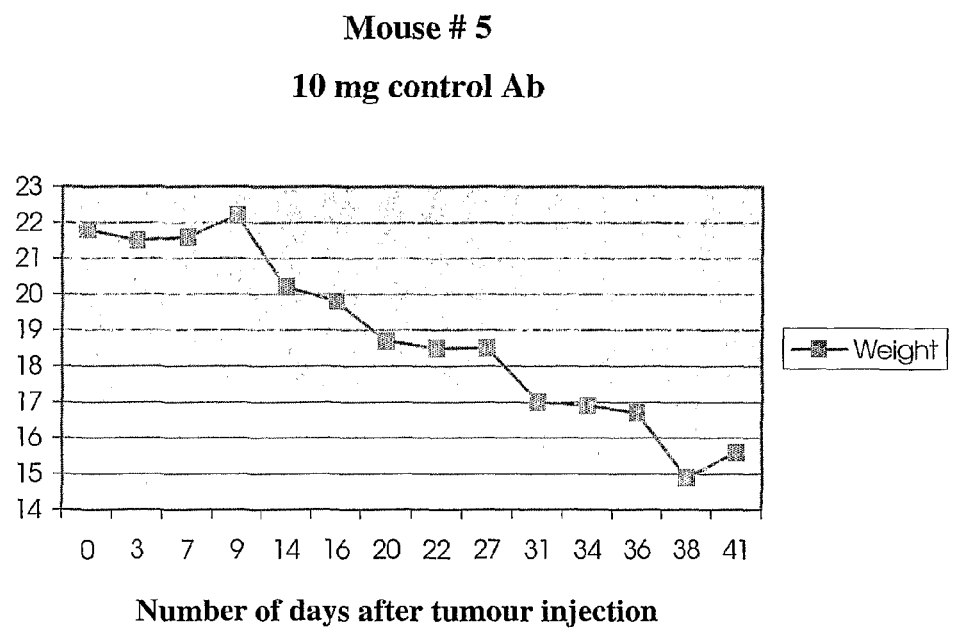

In the studies conducted with sheep anti-human MIC-1 IgG, it was found that 1 mg of sheep anti-human MIC-1 IgG made no difference to the weight of the mouse (data not shown), however 10 mg of anti-MIC-1 IgG (see FIG. 4A) induced a rapid weight gain in the respective tumour bearing nude mice (cf the results shown in FIG. 4B with 10 mg of control IgG). This weight gain peaked 5 to 6 days after administration of the antibodies, and then gradually the mice began to lose weight over the following 7 to 10 days.

Figure 5:
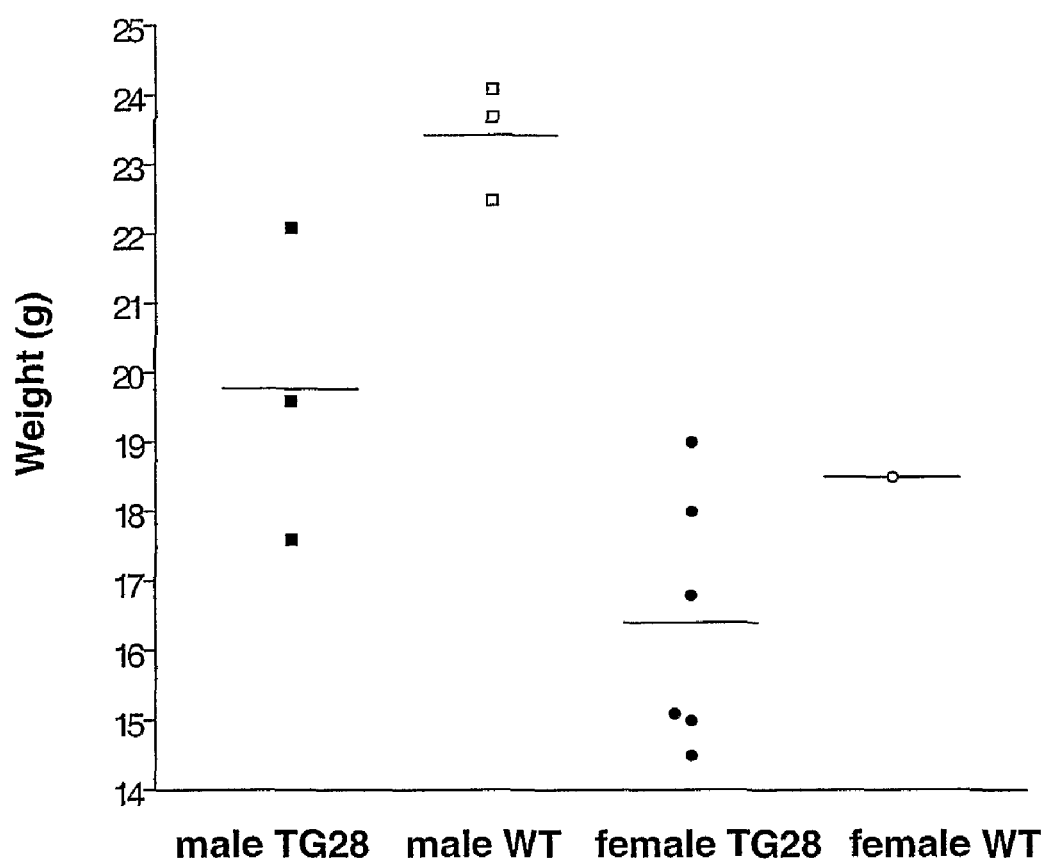
FIG. 5 provides the results of a weight loss assessment with a MIC-1 over-expressing transgenic (TG) mouse line min 28. Body weight was significantly reduced (P<0.001) in both male and female min 28 mice compared to congenic wild type litter mates (3 litters, 59 to 61 days of age).
Figure 6:
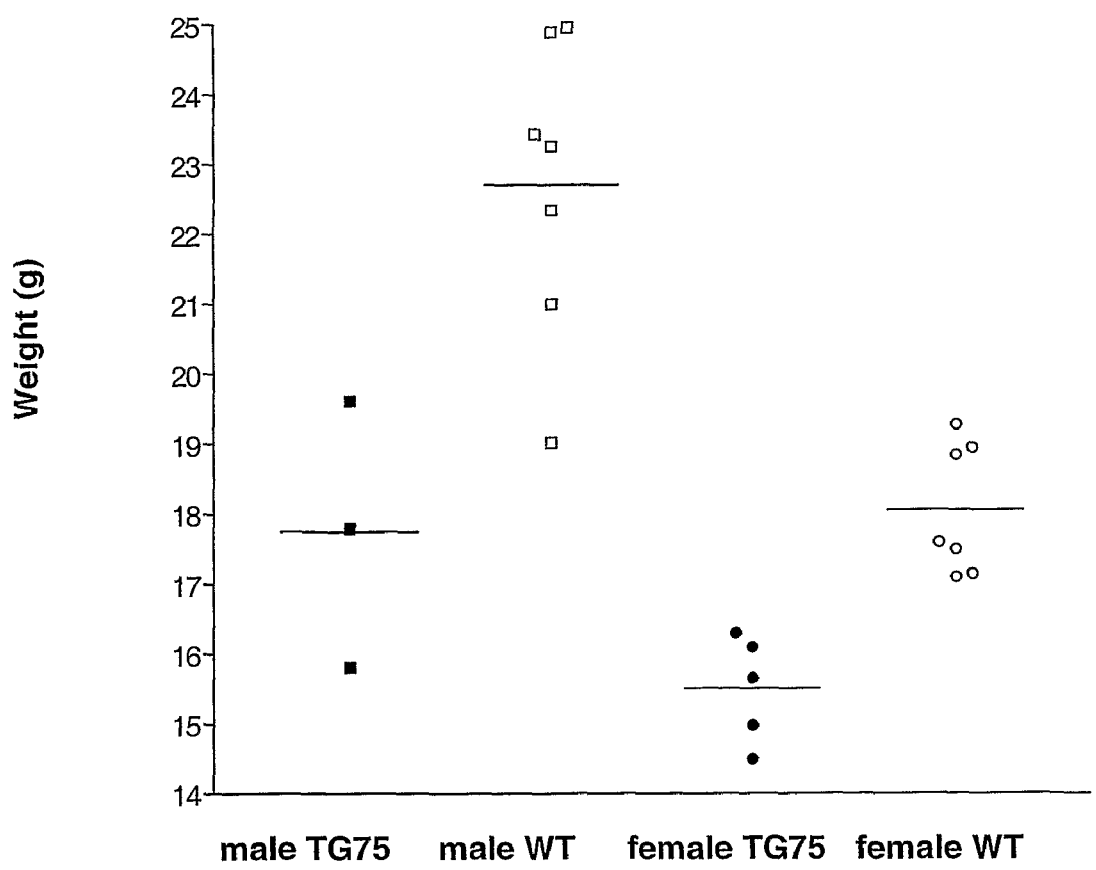
FIG. 6 provides the results of a weight loss assessment with a MIC-1 over-expressing transgenic (TG) mouse line min 75. Body weight was significantly reduced (P<0.001) in both male and female min 75 mice compared to congenic wild type (WT) litter mates (3 litters, 59 to 61 days of age).
Figure 7:
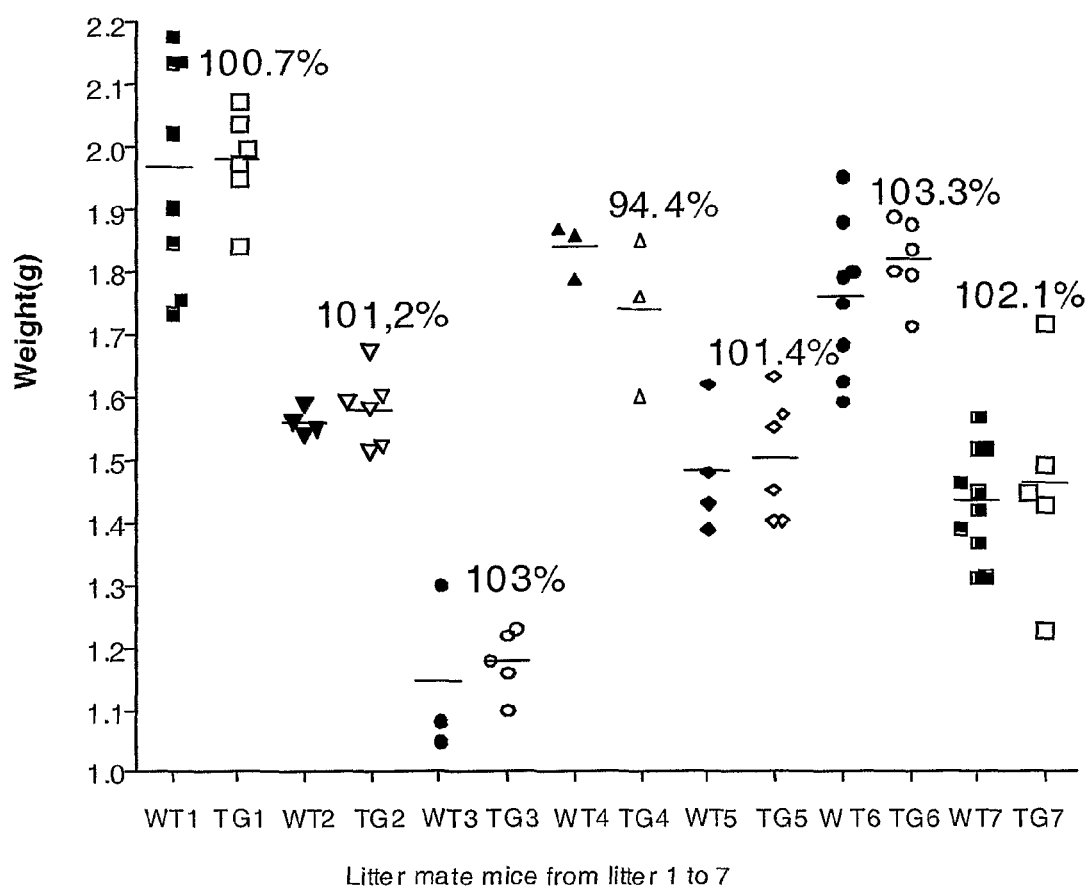
FIG. 7 shows a comparison of body weight (g), of wild type mice (filled symbols, WT) and heterozygous transgenic litter mate mice (TG, open symbols) from seven litters. The number indicates the average weight of heterozygous mice compared to their wild type litter mates within each litter. Newborn WT and TG mice (less than mice<48 h old) are not significantly different in bodyweights.

The results of the weight loss assessment in the transgenic mice lines min 28 and min 75 are shown in FIGS. 5 to 7 and indicate that these mice are also substantially smaller than their wild type congenic littermates. In these mice, weight at birth is equal and differences in weight start appearing after the first few weeks of life.

Discussion

The observed weight loss was very dramatic in some mice and was found to be related to the serum level of tumour-derived human MIC-1. The mice transduced with a DU145 clone over expressing mature human MIC-1 had by far the highest levels of serum MIC-1 and these mice lost weight at a dramatic rate. Observation of animal behaviour, indicated that a major reason for this, was a dramatic reduction in food ingestion by these mice. The finding that the weight loss could be reversed by administration with sheep anti-MIC-1 IgG (but not control IgG) demonstrates that the weight loss was due to MIC-1. This was corroborated by the weight loss assessment with the transgenic mice lines min 28 and min 75. In these mice, which have markedly elevated serum MIC-1 levels even though MIC-1 expression is macrophage-specific, a significant weight differential was observed as compared to congenic wild type mice. This weight loss effect occurred after birth, since both the transgenic mice lines and their congenic wild type litter mates had identical birth weights (ie as measured 24 hours after birth).

EXAMPLE 3

Figure 8A:
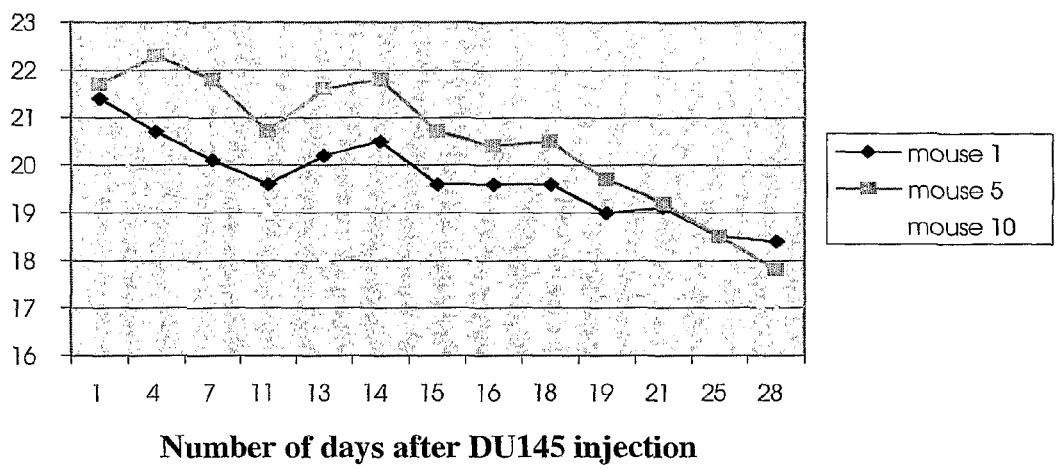
FIG. 8 shows that administration of a monoclonal antibody (MAb26) to human MIC-1 can reverse the weight loss in nude mice xenografted with human DU145 cells which have been transduced to over-express MIC-1 using a construct of mature human MIC-1 (no propeptide). Mice injected with DU145 cells over expressing MIC-1 started to lose weight rapidly. Administration of a single injection of MAb26, in amounts between 0.1 and 1 mg, at day 11, caused in increase in weight, the magnitude of which, and the duration of which, increased with increasing amounts of MAb26 (A-C). There was no effect of MAb26 on tumour growth (D-F). Untreated mice (G) and mice treated with PBS buffer alone (H) rapidly and continuously lost weight over the course of the experiment. Weight (g) on the vertical axis.
Figure 8B:
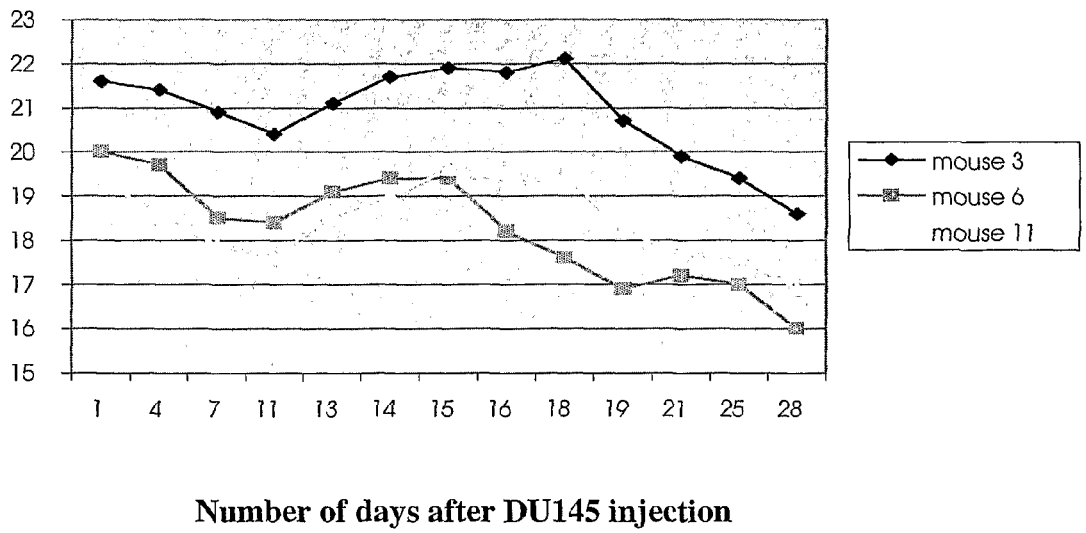
Figure 8C:
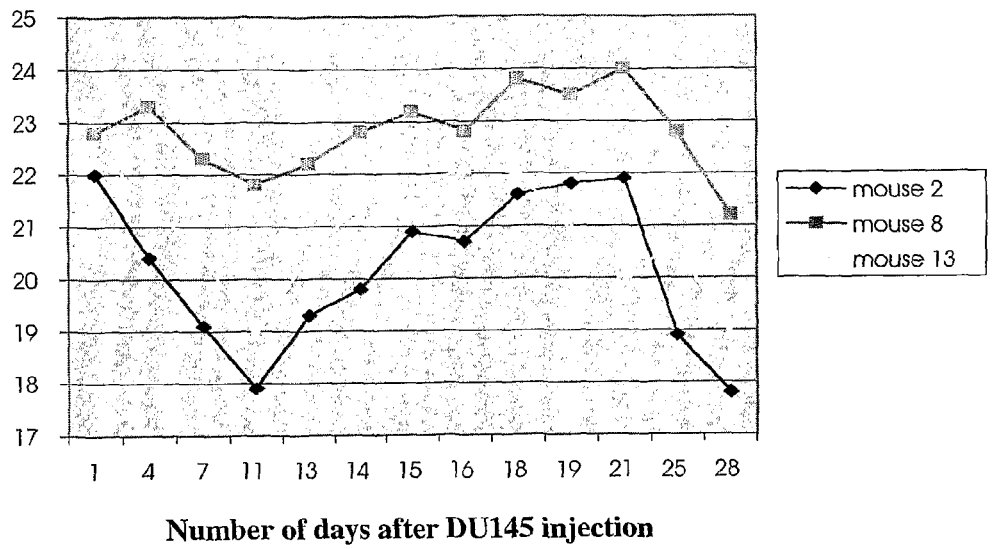
Figure 8D:
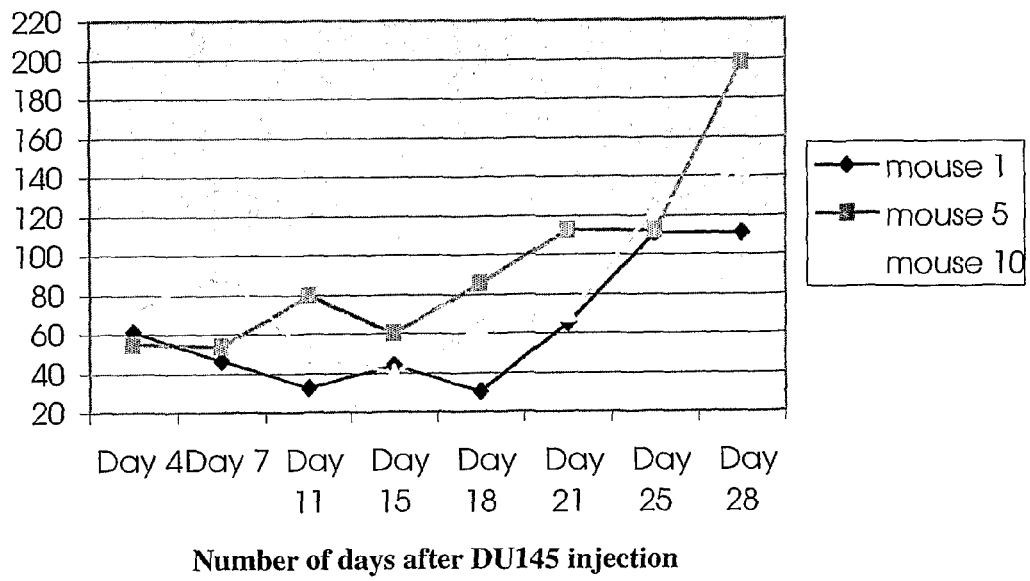
Figure 8E:
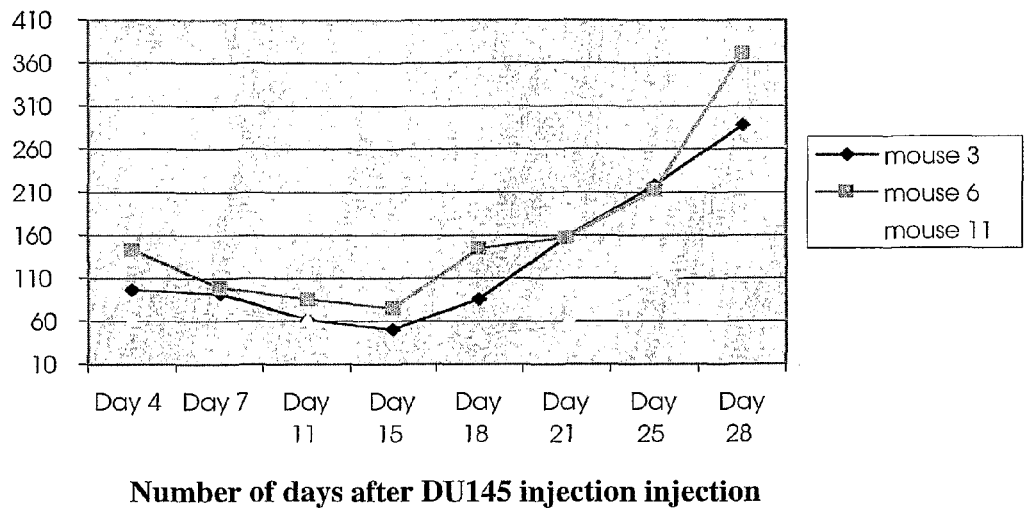
Figure 8F:
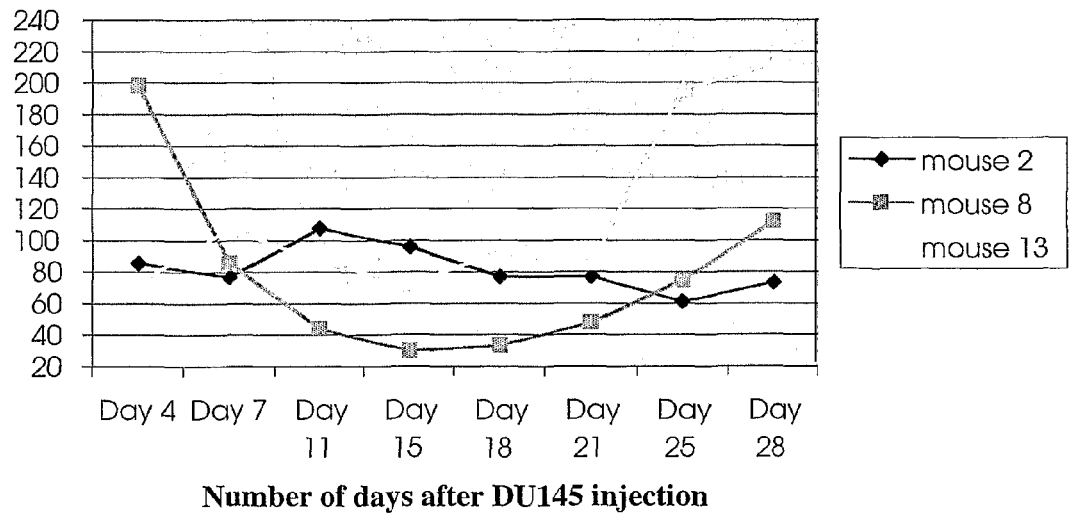
Figure 8G:
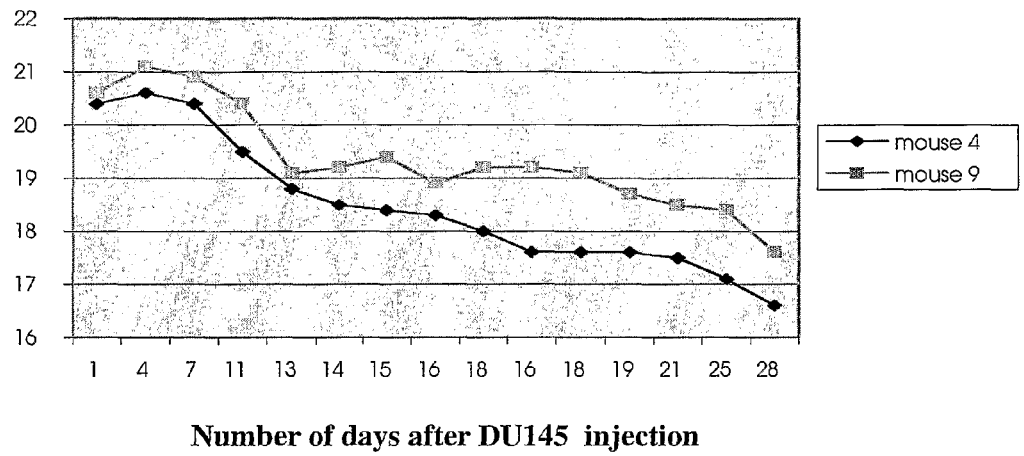
Figure 8H:
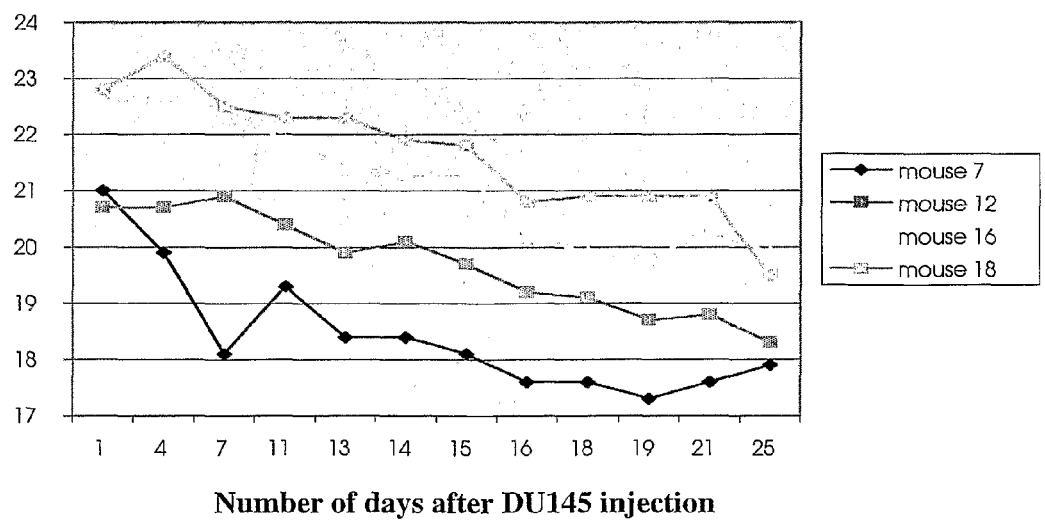

Weight Loss Associated with MIC-1 Secreting Tumour is Reversed by Administration of an Anti-MIC-1 Monoclonal Antibody Results and Discussion A xenograft model was established in nude mice (as described above) into whose flanks were injected either DU145 cells engineered to over-express mature MIC-1. Mice injected with DU145 cells over expressing MIC-1 started to lose weight rapidly. Administration of a single injection of a monoclonal antibody to MIC-1 (MAb26), in amounts between 0.1 and 1 mg, at day 11, caused an increase in weight, the magnitude of which, and the duration of which increased with increasing amounts of MAb26 (FIGS. 8A-C). At the highest dose of approximately 1 mg, the weight had risen to the pre-xenograft level and took approximately 17 days to decrease again to the same weight as when the antibody was first administered. There was no effect of MAb26 on tumour growth (FIGS. 8D-F) and untreated mice (FIG. 8G) and mice treated with phosphate buffered saline (FIG. 8H) (PBS) alone, rapidly and continuously lost weight over the duration of the experiment.

EXAMPLE 4

Effect on Food Intake in Mouse Xenograft Model

Materials and Methods

A xenograft model was established in nude mice (as described above) into whose flanks were injected either DU145 cells engineered to over-express mature MIC-1, or bear a control plasmid. On day 8 after injection of the DU145 cells over-expressing MIC-1, when the average tumour volume was 56 mm$^3$ and the average weight loss 7%, food intake was measured for 3 consecutive 24 hour time periods. The mice were left in groups of 5 per cage. Food placed into the hopper and litter were weighed at time point 0. After 24 hours, food consumed was estimated by subtracting refusal and spillage from food put into the hopper. Food intake for the control mice was measured in the same way, but on day 21 after tumour injection when the tumour volume had reached an average of 70 mm$^3$.

Results

Figure 9:
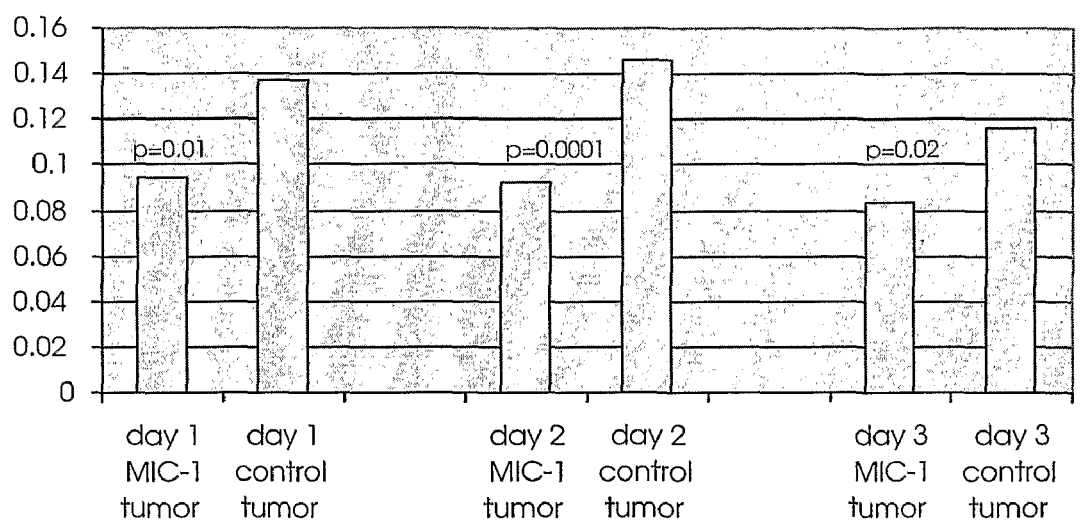
FIG. 9 shows a comparison of food intake, daily over 3 successive days, in nude mice xenografted with human DU145 cells which have been transduced to over-express MIC-1 using a construct of mature human MIC-1 (no propeptide) and control mice receiving DU145 cells transduced with a control construct.
Figure 10:
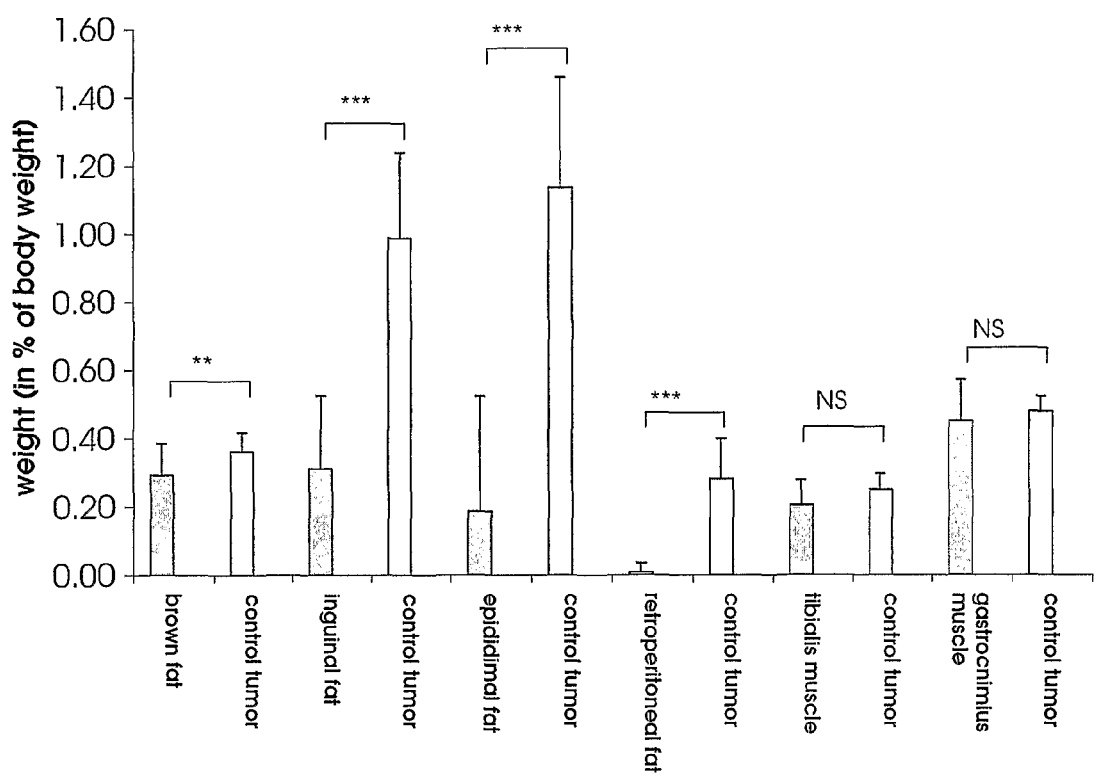
FIG. 10 shows a comparison of fat pad and muscle weights in nude mice xenografted with human DU145 cells which have been transduced to over-express MIC-1 using a construct of mature human MIC-1 (no propeptide) and control mice receiving DU145 cells transduced with a control construct. MIC-1 bearing DU145 expression tumours are represented by solid bars and the open bars represent mice bearing control tumours. Statistical comparison was undertaken using T test and the number of stars indicates increasing statistical significance from p=0.003 to p<0.0001. There was a marked decrease in the weight of body fat in inguinal fat, epididimal fat and retroperitoneal fat. There was no significant difference in the muscle weight between the two groups of mice. NS=not significant p<0.01 *p<0.001.

Mice injected with DU145 over-expressing MIC-1 ate significantly less food (about 30%) on day 1, 2 and 3 (p=0.01, 0.0001 and 0.02) than the control mice (FIG. 9). A direct measurement of fat mass in these mice indicated that MIC-1 over-expression was associated with a marked reduction in fat mass in the epididymal, inguinal, and retroperitoneal areas with no reduction in mass in two representative muscles (FIG. 10).

EXAMPLE 5

Measurement of Serum Metabolic Markers in Mouse Xenograft Model

Materials and Methods

A xenograft model was established in nude mice (as described previously) into whose flanks were injected either DU145 cells engineered to over-express MIC-1 or control DU145 cells. At 11-16 days after injection of the DU145 tumour cells over-expressing MIC-1 and 21-30 days after injection of the control tumour, when tumour volumes had reached 100-200 mm$^3$, and, or the mice had lost approximately 18% body weight, the mice were sacrificed. From previous experiments it is known that serum levels of tumour derived human MIC-1 are between 15 and 58 ng/ml. Serum was collected by cardiac puncture and assayed for the metabolic markers using commercial immunoassays. Statistical comparison was undertaken using the student T test.

Results and Discussion

Measurement of a range of metabolic markers in mice demonstrated a statistically significant reduction in MIC-1 over-expressing tumor mice of triglyceride and free fatty acids as well as glucagon and IGF-1 (data not shown). There was also a reduction in leptin levels that is consistent with reduction in fat mass, an indication that it is very unlikely that MIC-1 reduced food intake is mediated by MIC-1 stimulation of leptin. The difference for glucose was just short of statistical significance at p=0.053. These finding are largely in keeping with starvation and loss of fat mass.

EXAMPLE 6

Measurement of Fat Pad and Muscle Weight in Mouse Xenograft Model

Materials and Methods

A xenograft model was established in male nude mice (as described above). Into the flanks of 20 mice were injected DU145 cells engineered to over-express MIC-1 and into 20 mice were injected DU145 cells transduced with a control plasmid. At 11-16 days after injection of the DU145 tumour cells over-expressing MIC-1 and 21-30 days after injection of the control tumour, when tumour volumes had reached 100-200 $mm^3$, and, or the mice had lost approximately 18% body weight, the mice were sacrificed. Interscapular brown adipose tissue, inguinal, epididymal, and retroperitoneal fat and also tibialis and gastrocnemius muscle carefully dissected, removed and weighed and the weight was corrected for body weight.

Results and Discussion

There was no reduction in brown fat but there was a marked decrease in the weight of body fat in inguinal fat, epididymal fat and retroperitoneal fat (FIG. 10). There was no significant difference in the muscle weight between the two groups of mice (FIG. 10). However, using more sensitive total lean body mass analysis using the PIXImus imager (GE Lunar) indicated that there was an overall reduction in lean body mass. It also confirmed a much greater reduction in total fat mass and abdominal fat mass.

EXAMPLE 7

MIC-1 Transgenic Mice

Results and Discussion

Transgenic mice were engineered to over-express MIC-1 from monocytoid cells under the control of the c-fms promoter. These mice have systemically elevated MIC-1 levels, appear well and breed normally. They are indistinguishable from wild type mice but do show a significant growth retardation starting at about 3 weeks and into adulthood (FIG. 5-7). This effect was observed in two independent transgenic lines called min 75 and min 28.

Figure 11:
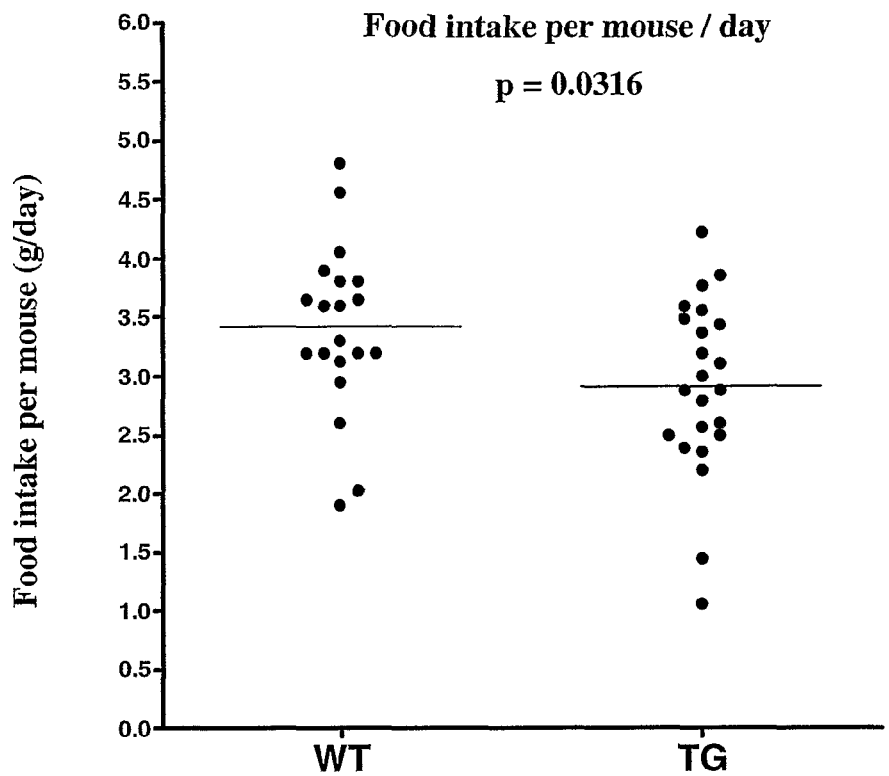
FIG. 11 shows food intake in MIC-1 transgenic mice compared to wild type controls. 5 wild type (WT) and 6 transgenic (TG) mice were individually housed in cages, and left for 48 hours to adjust to the single housing. Food placed in the hopper was weighed at time point zero. Every 24 hours, food consumed was estimated by subtracting the refusal and the spillage from the weight of the food put into the hopper. Food intake was measured over four, separate 24 hour periods. Food intake per mouse/day was significantly greater in WT animals (p<0.03) (A). However, this difference disappeared when the food intake was corrected for the body weight of the mouse (B).
Figure 11:
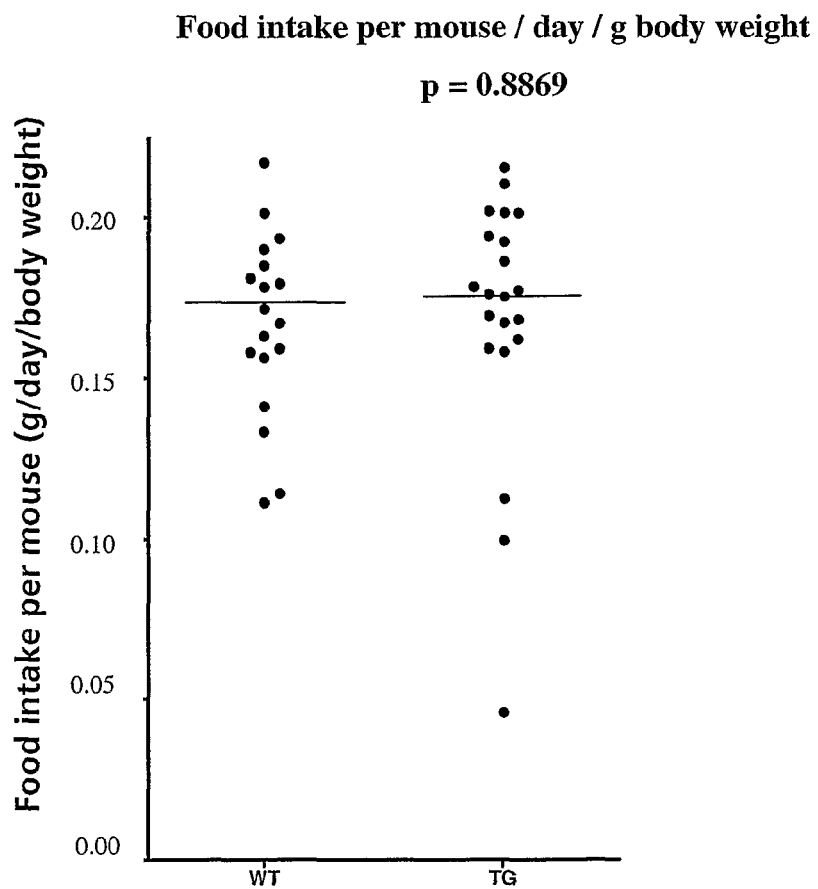

Like the tumour xenograft mice, the MIC-1 over-expressing transgenic mice ate significantly less than their wild type counterparts, but this difference disappears if the food intake is corrected for mouse weight (FIG. 11). It is believed that increased MIC-1 levels from birth result in decreased food intake which results in decreased size and the reach an equilibrium in which their size is appropriate for their reduced food intake. Measurement of the same metabolic markers in the transgenic animals, as in the tumour xenografted mice only showed a significant difference in IGF-1 levels, which are reduced in the MIC-1 transgenic mice.

Figure 12:
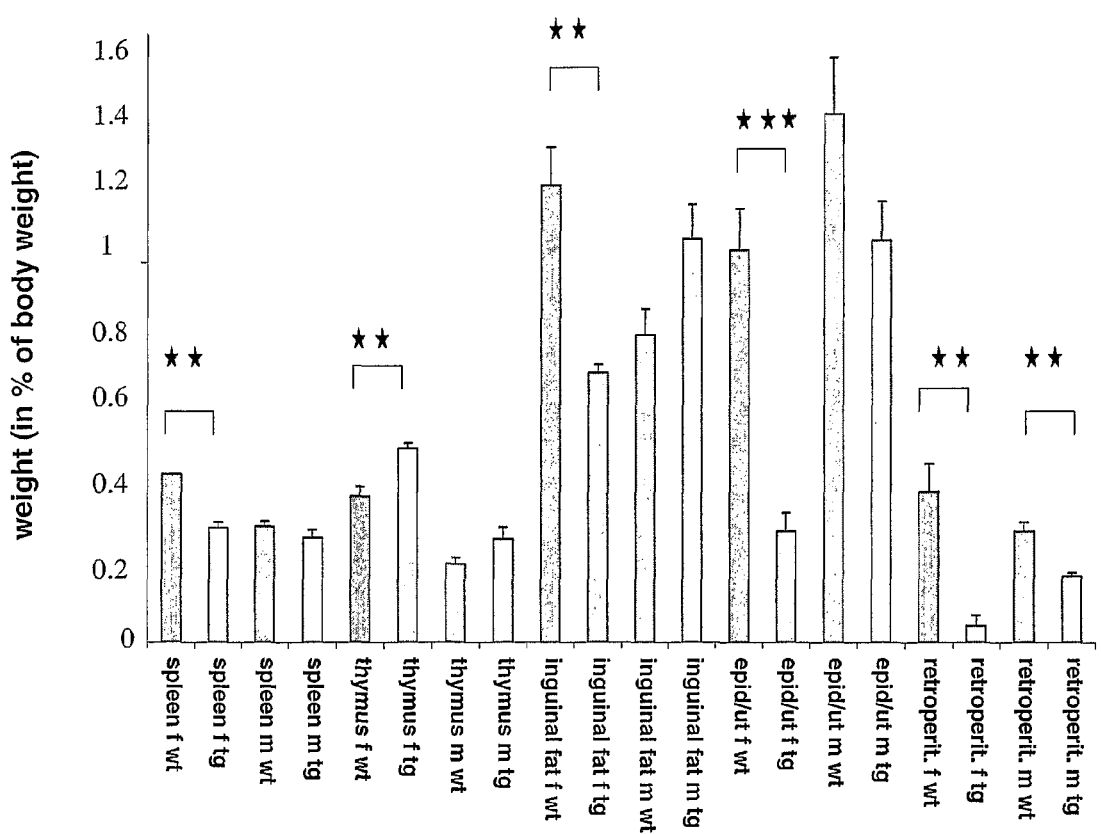
FIG. 12 shows the weights of organs from MIC-1 transgenic (TG) mice and wild type (WT) mice. Abbreviations: m=male, f=female, epid=epidydimal, ut=uterine, retroperit=retroperitoneal. p<0.01 *p<0.001.

Measurement of fat mass in inguinal, epididymal/uterine and retroperitoneal areas shows a decreased fat mass in the over expressing transgenic mice that is more prominent in female compared to male mice (FIG. 12). Beside a smaller spleen and a larger thymus, all three analysed fat pads were reduced in size. In absolute terms, there was no difference between the weights of WT versus TG thymus.

EXAMPLE 8

Control of Serum MIC-1 Levels by Fetuin

The presence of serum MIC-1, at a mean concentration of 450 pg/ml in all individuals, suggests that like some other TGF-β superfamily cytokines, MIC-1 may bind to one or more circulating modulators. The glycoprotein, fetuin is widely expressed in cells and tissues and is present in blood serum. The following investigation was made to determine whether MIC-1 may interact with this glycoprotein.

Materials and Methods

Purified recombinant, mature MIC-1 (in 0.1% BSA) was incubated with fetuin-coated agarose beads. The beads were then washed and bound material analysed by SDS-PAGE followed by Western blotting with anti-MIC-1 antibody: Lane 1, purified recombinant MIC-1; Lane 2, MIC-1 bound to fetuin beads; Lane 3, fetuin beads only; Lane 4, MIC-1 incubated with agarose beads only.

Results

Figure 13:
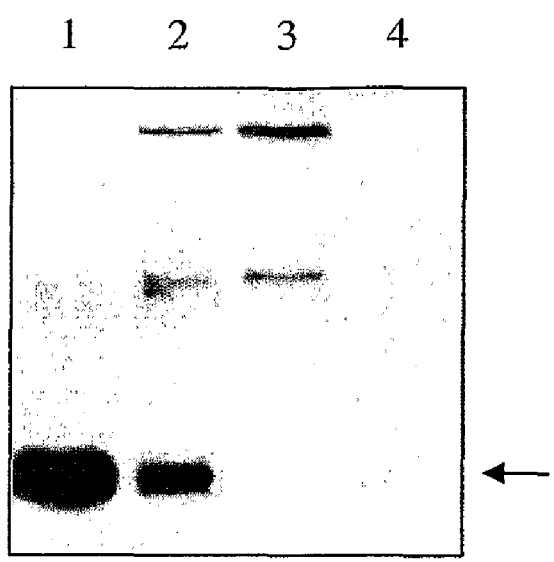
FIG. 13 shows the results of assays for MIC-1 binding to fetuin. Purified recombinant MIC-1 (in 0.1% BSA) was incubated with fetuin-coated agarose beads. The beads were then washed and bound material analysed by SDS-PAGE followed by Western blotting with anti-MIC-1 antibody. Lane 1, purified recombinant MIC-1; lane 2, MIC-1 bound to fetuin beads; lane 3, fetuin beads only; lane 4, MIC-1 incubated with agarose beads only. The arrow indicates the MIC-1 bands.

The results, shown in FIG. 13, clearly indicate that mature MIC-1 interacts and binds with fetuin.

Discussion

As MIC-1 binds to fetuin, fetuin may offer an alternative to the administration of anti-MIC-1 antibodies for modulating functions mediated by serum MIC-1. For example, for modulating the inhibitory effects of serum MIC-1 on appetite, fetuin could be administered to a subject (eg a subject suffering from advanced cancer) by a suitable route (eg intravenous administration) so as to reduce the level of "free" MIC-1.

EXAMPLE 9

Analysis of MIC-1 Expression in Normal Mouse Brain

Results and Discussion

Figure 14A:
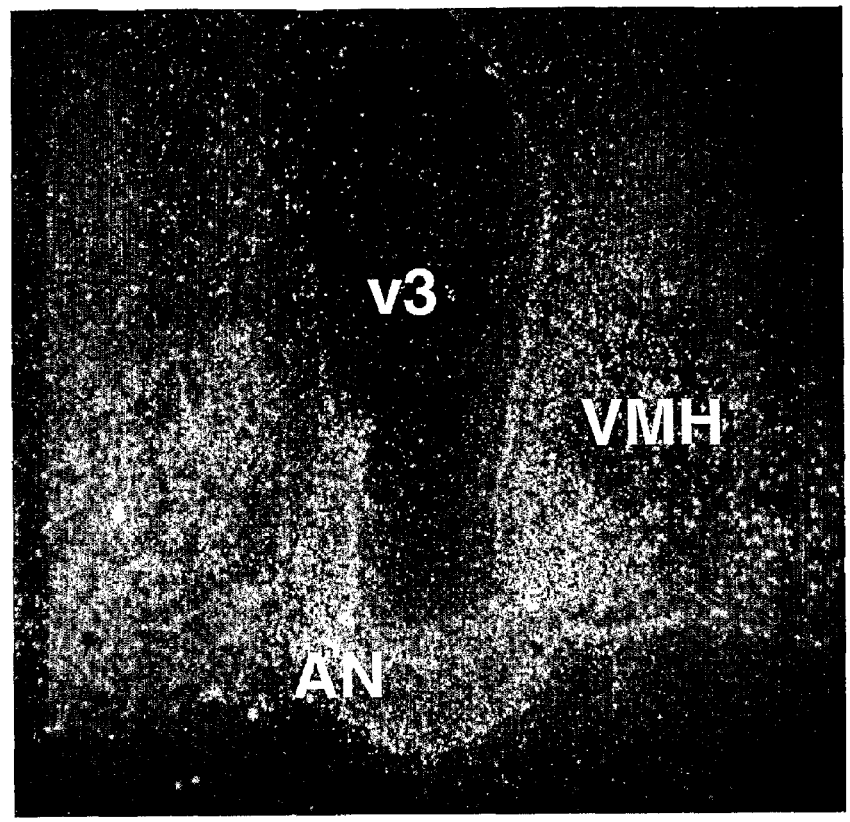
FIG. 14 sections of normal adult mouse brain in the region of the hypothalamus and the third ventricle (V3) were cut an subjected to (A) in situ hybridisation for MIC-1 using $^{35}$S-labelled RNA probe and autoradiography and (B) immunohistochemistry using in house affinity purified polyclonal antibodies to recombinant murine MIC-1. The sections show expression of MIC-1 mRNA and proteins in the region of the arcuate nucleus (ΔN) and paraventlicular region.
Figure 14B:
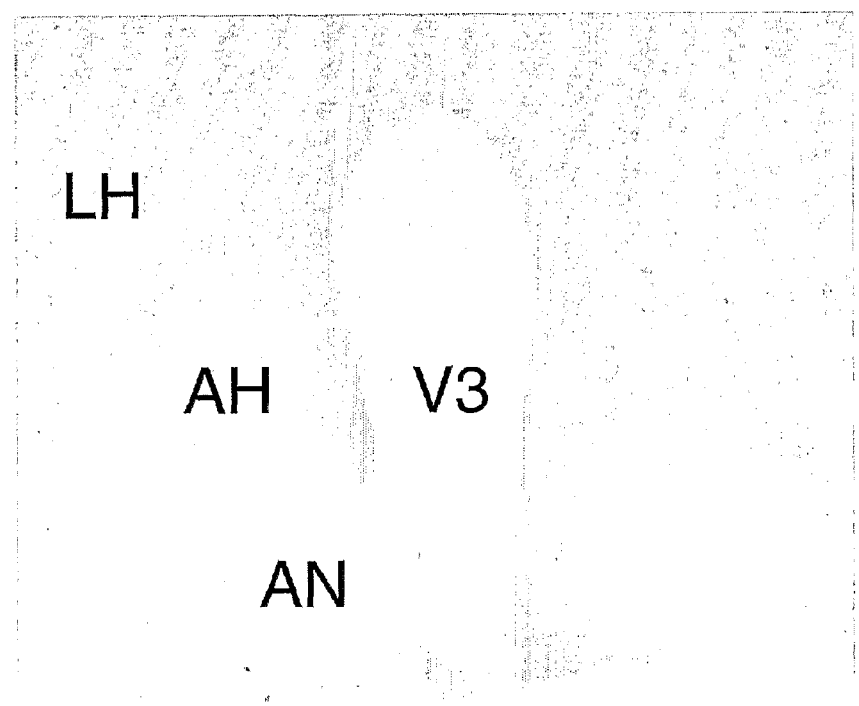

Food intake and appetite are controlled by a complex array of mechanisms, many of which are located within the central nervous system. The area within the nervous system controlling many basal bodily functions such a appetite and body temperature are localised within the area of the hypothalamus. In the case of appetite, many of the complex factors regulating this process are localised to the arcuate nucleus of the hypothalamus and many of the mediators and receptors for mediators such as neuropeptide Y are localised in this area. The blood brain barrier in this area is also leaky and it is one of the very limited areas of the brain where there is an opportunity for systemic molecules to cross the blood brain barrier and act directly in the brain. It is considered that MIC-1 is able to exert a direct effect on the acuate nucleus and hypothalamus by this mechanism. However, MIC-1 is also expressed within this region of the normal mouse brain (FIG. 14). It does not represent diffusion of circulating MIC-1 as indicated by studies of in situ bybridisation which demonstrate co-localisation of MIC-1 mRNA and protein in the area of the acuate nucleus, periventricular area and paraventricular hypothalamus. The localisation of MIC-1 in those areas of normal brain, strongly associated with functions such as appetite control, provides a strong argument for the role of MIC-1, both from the peripheral circulation, and endogenously produced within the brain, in controlling this important function.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Bootcov M R, Bauskin A, Valenzuela S M, Moore A G, Bansal M, He C, Zhang B P, Donnellan M, Mahler S, Pryor K, Walsh B, Nicholson R, Fairlie D F, Por S B, Robbins J M, Breit S N. MIC-1, a novel macrophage inhibitory cytokine, is a divergent member of the TGF-β superfamily cluster. Proc Natl Acad Sci USA 1997: 94:11514-11519.
2. Breit S N, Bootcov M R. "Novel TGF-beta like cytokine", International Patent Application No PCT/AU96/00386 (WO 97/00958).
3. Fairlie W D, Zhang H—P, Brown P K, Russell P K, Bauskin A R, Breit S N. Expression of a TGF-β superfamily protein, Macrophage Inhibitory Cytokine-1, in the yeast *Pichia pastoris*. Gene 2000: 254:67-76.
4. Moore A G, Brown D A, Fairlie W D, Bauskin A R, Brown P K, Munier M L C, Russell P K, Salamonsen L A, Wallace E M, Breit S N.TGF-β superfamily cytokine MIC-1 is present in high concentrations in the serum of pregnant women. J Clin Endocrinol Metab 2000: 85:4781-88.
5. Fairlie W D, Russell P K, Moore A G, Zhang H P, Brown P K, Breit S N. Epitope mapping of the Transforming Growth Factor-□ superfamily protein, MIC-1: Identification of at least five distinct epitope specificities. Biochemistry 2001: 40:65-73
6. Breit S N et al. "Diagnostic assay and method of treatment involving macrophage inhibitory cytokine-1 (MIC-1)", International Patent Application No PCT/AU01/00456 (WO 01/81928).
7. Fairlie W D, Moore A G, Bauskin A R, Russell P K, Zhang H P, Breit S N. MIC-1 is a novel TGF-β superfamily cytokine associated with macrophage activation. J Leukocyte Biol 1999; 65:2-5.
8. Koniaris L G. Induction of MIC-1/growth differentiation factor-15 following bile duct injury. J Gastrointest Surg 2003 Nov. 7(7):901-5.
9. Welsh J B, Hampton G M. Analysis of Gene Expression Identifies Candidate Markers and Pharmacological Targets in Prostate Cancer. Cancer Res 2001: 61:5974-5978.
10. Buckhaults P. Vogelstein B, Kinzler K W. Secreted and cell surface genes expressed in benign and malignant colorectal tumors. Cancer Res 2001: 61:6996-7001.
11. Welsh J B, Sapinoso L M, Kern S G, Brown D A, Liu T, Bauskin A R, Ward R L, Hawkins N J, Quinn D I, Russell P J, Sutherland R L, Breit S N, Moskaluk C A, Frierson, H A Jr. and Hampton G M. Large-Scale Delineation of Secreted Protein Biomarkers Overexpressed in Cancer Tissue and Serum. Proc Natl Acad Sci USA 2003: 100:3410-3415.
12. Kannan K, Amariglio N, Rechavi G, Givol D. 2000 Profile of gene expression regulated by induced p53: connection to the TGF-beta family. FEBS Lett 470:77-82.
13. Pei-Xiang Li, et al. Placental Transforming Growth Factor-b Is a Downstream Mediator of the Growth Arrest and Apoptotic Response of Tumour Cells to DNA Damage and p53 Overexpression. J Biol Chem 2000: 275:20127-20135.
14. Yang H, Filipovic Z, Brown D, Breit S N, Vassilev L T. Macrophage inhibitory cytoline-1: a novel biomarker for p53 pathway activation. Mol Cancer Ther 2003: Oct. 2(10):1023-1029.
15. Albertoni M, Shaw P H, Nozaki M, Godard S, Tenan M, Hamou M-F, Fairlie D W, Breit S N, Paralkar V M, de Tribolet N, Van Meir E G, Hegi M E. Anoxia induces macrophage inhibitory cytokine-1 (MIC-1) in glioblastoma cells independently of p53 and HIF-1. Oncogene 2002: 27:4212-4219.
16. Brown D A, Bauskin A R, Fairlie W D, Smith M D, Liu T, Xu N and Breit S N. An antibody based approach to high volume genotyping for MIC-1 polymorphism. Biotechniques 2002: 33(1):118-20, 122, 124 passim.
17. Liu T, Bauskin A R, Zaunders J, Brown D A, Pankurst S, Russell P J, Breit S N. MIC-1 reduces cell adhesion and induces apoptosis in prostate cancer cells. Cancer Res 2003:63:5034-5040.
18. Koopmann J, Buckhaults P, Brown D A, Zahurak M L, Sato N, Sokoll L, Chan D W, Yeo C J, Hruban R H, Breit S N, Kinzler K W, Vogelstein B, Goggins M. Serum MIC-1 as a Marker of Pancreatic and other Periampullary Cancers. Clin Cancer Res (in press).
19. Baek S J et al. Cyclooxygenase inhibitors regulate the expression of a TGF-beta superfamily member that has proapoptotic and antitumorigenic activities. Mol Pharmacol 2001: 59:901-908.
20. Brown D A, Ward R L, Buckhaults P, Liu T, Romans K E, Hawkins N J, Bauskin A R, Kinzler K W, Vogelstein B, Breit S N. MIC-1 serum level and genotype: Associations with progress and prognosis of colorectal carcinoma. Clinical Cancer Research 2003: 9:2642-2650.
21. Lee D H, Yang Y, Lee S J, Kim K Y, Koo T H, Shin S M, Song K S, Lee Y H et al. Macrophage inhibitory cytokine-1 induces the invasiveness of gastric cancer cells by up-regulating the urokinase-type plasminogen activator system. Cancer Res 2003: Aug. 1; 63(15):4648-4655.
22. Pluckthun A, Antibody engineering: advances from the use of *Escherichia coli* expression systems. Bio/Technology 1991:9:545-551.
23. Vassilev L T, Vu B T, Graves B, Carvajal D, Podlaski F, Filipovic Z, Kong N, Kammlott U, Lukacs C, Klein C, Fotouhi N, Liu E A. In vivo activation of the p53 pathway by small-molecule antagonists of MDM2. Science 2004: February 6; 303(5659):844-848.
24. Bauskin A R, Brown D A, Junankar S, Rasiah K K, Eggleton S, Hunter M, Liu T, Smith D, Kuffner T, Pankhurst, G J, Johnen, H, Russell P J, Barret W, Stricker P D, Grygiel J J, Kench J G, Henshall S M, Sutherland R L, Breit S N. The propeptide mediates formation of stromal stores of PROMIC-1: role in determining prostate cancer outcome. Cancer Res 2005: Mar. 15; 65(6):2330-2336.

The invention claimed is:

1. A method for increasing appetite and/or body weight in a subject suffering from decreased appetite and/or body weight loss associated with elevated expression or amounts of MIC-1, said method comprising administering to said subject an effective amount of an anti-MIC-1 antibody or MIC-1 binding fragment thereof optionally in admixture with a pharmacologically-acceptable carrier and/or excipient.

2. A method according to claim 1, wherein said anti-MIC-1 antibody or MIC-1 binding fragment thereof decreases the amount of endogenous MIC-1 in said subject.

3. A method according to claim 1, wherein said anti-MIC-1 antibody or MIC-1 binding fragment thereof inhibits the activity of endogenous MIC-1 in said subject.

4. A method according to claim 1 wherein said anti-MIC-1 antibody is a humanised monoclonal anti-MIC-1 antibody.

5. A method according to claim 1, wherein the subject is suffering from decreased appetite and/or weight loss associated with advanced cancer.

6. A method for decreasing appetite and/or body weight in a subject, said method comprising administering to said subject an effective amount of MIC-1, optionally in admixture with a pharmacologically-acceptable carrier and/or excipient.

7. A method according to claim 6, wherein the subject is suffering from obesity.

8. A method for assessing the effect of an agent on the appetite and/or body weight of a subject, said method comprising administering said agent to said subject and detecting any increase or decrease in the amount of MIC-1 in said subject, wherein an increase in the amount of MIC-1 indicates that said agent decreases appetite and/or body weight in a subject and a decrease in the amount of MIC-1 indicates that said agent increases appetite and/or body weight in a subject.

9. A method for assessing the effect of an agent on the appetite and/or body weight of a subject, said method comprising the steps of:
    exposing a cell expressing MIC-1 to said agent,
    detecting any increase or decrease in the level of said expression of MIC-1,
    determining from an increase in the level of expression of MIC-1 that said agent decreases appetite and/or body weight in a subject and
    determining from a decrease in the level of expression of MIC-1 that said agent increases appetite and/or body weight in a subject.

10. A method according to claim 9, wherein the subject is suffering from obesity.

11. A diagnostic method comprising the steps of:
    selecting a subject suffering from decreased appetite and/or weight loss,
    determining the amount of MIC-1 present in the serum in said subject,
    determining from said amount whether MIC-1 is over-expressed,
    wherein MIC-1 over-expression in serum identifies the subject as being suitable for treatment by administering an anti-MIC-1 antibody or fragment thereof.

* * * * *